United States Patent [19]

Wedel

[11] 4,077,940
[45] Mar. 7, 1978

[54] THERMAL STABILIZATION OF POLYPYRROLIDONE AGAINST REVERSION TO MONOMER

[75] Inventor: Carroll J. Wedel, Walnut Creek, Calif.

[73] Assignee: Chevron Research Company, San Francisco, Calif.

[21] Appl. No.: 723,114

[22] Filed: Sep. 14, 1976

[51] Int. Cl.² .......................... C07F 9/48; C08K 5/53
[52] U.S. Cl. ................................ 260/45.7 P; 260/932
[58] Field of Search ........................ 260/45.7 P, 932

[56] References Cited
U.S. PATENT DOCUMENTS 3,078,248   2/1963   Ber ................................. 260/45.7 P
3,787,529   1/1974   Benghiat ......................... 260/45.7 P
3,962,175   6/1976   Hofer et al. ..................... 260/45.7 P
3,962,377   6/1976   Spivack ........................... 260/45.7 P
3,976,619   8/1976   Morgan et al. .................. 260/45.7 P

OTHER PUBLICATIONS

Sandoz Technical Bulletin – Sandostab P-EPQ (1975).

Primary Examiner—Donald E. Czaja
Assistant Examiner—H. H. Fletcher
Attorney, Agent, or Firm—D. A. Newell; DeJonghe T. G.; L. S. Squires

[57] ABSTRACT

Certain aryl esters of bis-arylphosphonous acid are thermal stabilization additives for solid polypyrrolidone at the melt temperature.

3 Claims, No Drawings

THERMAL STABILIZATION OF POLYPYRROLIDONE AGAINST REVERSION TO MONOMER

BACKGROUND OF THE INVENTION

Poly-2-pyrrolidone is the source of a useful synthetic fiber for the textile industry. The melt-spinnable white solid polymer is produced by the alkaline-catalyzed polymerization of 2-pyrrolidone in the presence of carbon dioxide (see U.S. Pat. No. 3,721,652). Polypyrrolidone so-produced is melt-spun into filaments by extrusion from multi-hole spinnerets. In melt-spinning, the polymer composition is extruded in a molten condition at a temperature which is generally greater than about 270° C, and extruder temperatures, i.e., extruder screw barrel temperatures, of about 280° C and higher. The extrusion must be carried out with care because of the tendency of the polymer to thermally degrade and revert to monomer. Degradation produces an unacceptable extrudate containing foam or bubbles. If extrusion is attempted at an appreciably lower temperature to avoid thermal decomposition, or at higher extruder screw rpm to decrease the residence time at the extruder temperature, excessive torque must be developed in the extruder screw, the screw barrel temperature increases further, and the pressure at the spinneret increases and may fluctuate to yield an inconsistent product. Consequently, in order to melt extrude polypyrrolidone efficiently, one may either seek to increase the thermal stability of the polymer, or to improve the extrudability of the polymeric composition, by the use of additives.

SUMMARY OF THE INVENTION

The thermal stability of poly-2-pyrrolidone at the melt temperature is appreciably improved by the addition of aryl esters of bis-arylphosphonous acid, preferably of the formula

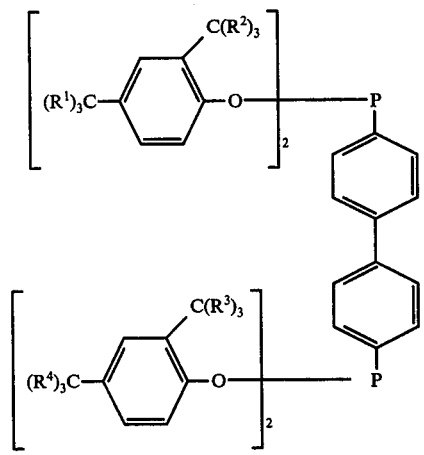

wherein $R^1$, $R^2$, $R^3$ and $R^4$ are lower alkyl groups. The poly-2-pyrrolidone composition comprises a major amount of normally solid poly-2-pyrrolidone and a thermal stabilizing amount of said aryl ester of arylphosphonous acid.

BRIEF DESCRIPTION OF PREFERRED EMBODIMENTS

A useful synthetic fiber is produced by the melt extrusion at extruder temperatures in excess of about 270° C of a composition comprising a major amount of polypyrrolidone produced by the alkaline-catalyzed polymerization of 2-pyrrolidone in the presence of carbon dioxide, and a minor amount of an aryl ester of bis-arylphosphonous acid having the following formula.

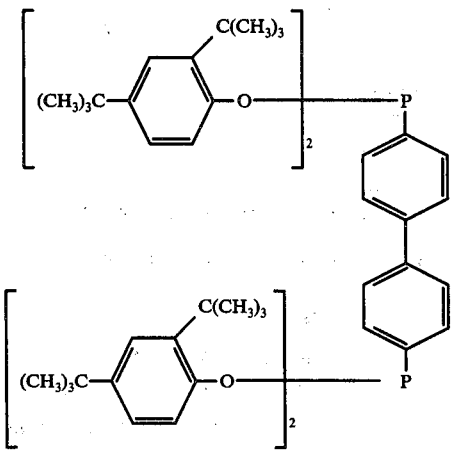

The addition of said ester in amounts of 0.5–5 weight percent appreciably improves the thermal stability of polypyrrolidone. The ester appreciably inhibits the degradation of the polymer to monomer at melt temperatures in excess of 260° C.

The preferred thermal stabilizing additive of the present invention is 4,4′-bis[O,O-di(2,4-di-t-butylphenyl)-phosphono]diphenylene, or tetrakis(2,4-ditert-butyl-phenyl)-4,4′-biphenylene diphosphonite, which is available under the trade name Sandostab P-EPQ (marketed by Sandoz Ltd.). The degradation of polypyrrolidone to monomer is not believed to involve an oxidation. The "normally solid" poly-2-pyrrolidone of the present invention is polypyrrolidone having a weight average molecular weight in excess of about 5,000 and preferably in excess of about 50,000. The aryl ester of arylphosphonous acid is normally added to the solid polypyrrolidone by coating the pellets of the polymer with said ester before extrusion, but any convenient method may be used.

Thermal stabilization is determined, among other methods, by the measurement of weight loss by the solid polypyrrolidone polymer on a Mettler FP-1 hot stage at 269° C over a period of five minutes, with and without the presence of the additive. The monomer produced by this heat treatment is completely removed by overnight extraction with water. The weight difference between the starting polymer and the dry extracted polymer is the weight loss. The thermal stabilizing additive of the present invention produces an overall reduction in monomer loss of about 18% at 1 weight percent additive and of about 11% at 0.5 weight percent additive. In the testing of numerous additives, some of which were commercial antioxidants, many antioxidants showed an insignificant or deleterious effect within the range of less than ±10% change in monomer loss at 1 weight percent additive. The reduction in monomer loss from polypyrrolidone produced by small amounts of the stabilizer of this invention is exceptional. A surprising number of commercial additives produced a substantial increase in monomer loss, including other phosphorus containing compounds such as zinc dicyclohexyldithiophosphinate and certain phosphine oxides. The results are exemplified in the following table.

TABLE

| Additive, % | Effect on Weight Loss[1], % |
|---|---|
| Ester[2], 0.3 | −9 |
| Ester[2], 2.0 | −23 |
| Zinc dicyclohexyldithiophosphinate, 0.2 | +24 |
| Triscyanoethylphosphine, 0.2 | +19 |

[1]Minus value indicates additive decreases the weight loss. Positive value indicates additive increases degradation of polypyrrolidone.
[2]4,4′-bis[O,O-di(2,4-di-t-butylphenyl)phosphono]-diphenylene.

What is claimed is:

1. A composition of matter comprising a major amount of a normally solid poly-2-pyrrolidone and a thermal stabilizing amount, effective to reduce the thermal degradation of said poly-2-pyrrolidone to monomer, of an additive having the formula

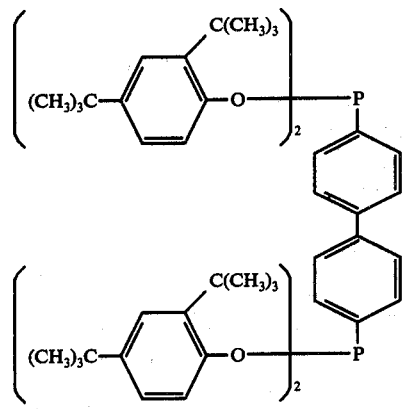

2. A composition of matter according to claim 1 wherein said additive comprises from about 0.5 weight percent to about 5 weight percent of said composition.

3. A process for extruding poly-2-pyrrolidone which comprises melt extruding the composition of claim 1 at extruder temperatures in excess of about 270° C.